United States Patent [19]
Anantaneni

[11] Patent Number: 6,166,281
[45] Date of Patent: Dec. 26, 2000

[54] ALKYLATION OF BENZENE TO FORM LINEAR ALKYLBENZENES USING FLUORINE-CONTAINING MORDENITES

[75] Inventor: Prakasa Rao Anantaneni, Austin, Tex.

[73] Assignee: Huntsman Petrochemical Corporation, Austin, Tex.

[21] Appl. No.: 09/175,078

[22] Filed: Oct. 19, 1998

Related U.S. Application Data

[63] Continuation-in-part of application No. 08/598,692, Feb. 8, 1996, Pat. No. 5,847,254, and application No. 08/879,745, Jun. 20, 1997, which is a division of application No. 08/598,695, Feb. 8, 1996, Pat. No. 5,770,782.

[51] Int. Cl.[7] .................................. C07C 2/66; C07C 2/68
[52] U.S. Cl. .................... 585/449; 585/302; 585/450; 585/455; 585/456; 585/460; 585/467
[58] Field of Search ................................ 585/302, 449, 585/450, 455, 456, 460, 467

[56] References Cited

U.S. PATENT DOCUMENTS

| | | | |
|---|---|---|---|
| 2,637,750 | 5/1953 | Smith et al. | 585/302 |
| 3,351,672 | 11/1967 | Adams et al. | 585/302 |
| 3,436,432 | 4/1969 | Mitsche | 585/467 |
| 3,551,510 | 12/1970 | Pollitzer et al. | |
| 3,594,331 | 7/1971 | Elliott, Jr. | |
| 3,630,965 | 12/1971 | Voorhies, Jr. et al. | |
| 3,702,312 | 11/1972 | Wilson | |
| 3,763,260 | 10/1973 | Pollitzer | |
| 3,849,340 | 11/1974 | Pollitzer | |
| 3,873,632 | 3/1975 | Pollitzer | |
| 3,933,983 | 1/1976 | Elliott, Jr. | |
| 4,232,177 | 11/1980 | Smith, Jr. | |
| 4,283,573 | 8/1981 | Young | |
| 4,301,317 | 11/1981 | Young | 585/455 |
| 4,307,254 | 12/1981 | Smith, Jr. | |
| 4,691,068 | 9/1987 | Resh | 585/323 |
| 4,849,569 | 7/1989 | Smith, Jr. | |
| 4,891,465 | 1/1990 | Taniguchi et al. | 485/463 |
| 4,918,244 | 4/1990 | Nelson et al. | |
| 4,950,834 | 8/1990 | Arganbright et al. | |
| 4,973,780 | 11/1990 | Johnson et al. | 585/467 |
| 4,978,807 | 12/1990 | Smith, Jr. | |
| 5,030,785 | 7/1991 | Huss, Jr. et al. | 585/456 |
| 5,034,564 | 7/1991 | Kocal | 585/467 |
| 5,043,506 | 8/1991 | Crossland | |
| 5,055,627 | 10/1991 | Smith, Jr. et al. | |
| 5,120,403 | 6/1992 | Smith, Jr. | |
| 5,146,026 | 9/1992 | Tejero et al. | 585/467 |
| 5,157,158 | 10/1992 | Tejero et al. | 585/467 |
| 5,175,135 | 12/1992 | Lee et al. | |
| 5,176,883 | 1/1993 | Smith, Jr. et al. | |
| 5,177,280 | 1/1993 | Junguin et al. | |
| 5,196,574 | 3/1993 | Kocal | 562/94 |
| 5,198,595 | 3/1993 | Lee et al. | |
| 5,204,064 | 4/1993 | Smith, Jr. | |
| 5,221,441 | 6/1993 | Smith, Jr. | |
| 5,233,111 | 8/1993 | Notte et al. | |
| 5,243,115 | 9/1993 | Smith, Jr. et al. | |
| 5,243,116 | 9/1993 | Lee et al. | |
| 5,262,576 | 11/1993 | Smith, Jr. | |
| 5,273,644 | 12/1993 | Wegerer | 208/66 |
| 5,313,005 | 5/1994 | Smith, Jr. et al. | |
| 5,334,793 | 8/1994 | Kocal | |
| 5,344,997 | 9/1994 | Kocal | 568/628 |
| 5,345,006 | 9/1994 | Smith, Jr. | |
| 5,368,691 | 11/1994 | Asselineau et al. | |
| 5,446,223 | 8/1995 | Smith, Jr. | |
| 5,574,198 | 11/1996 | Radici et al. | 585/323 |
| 5,770,782 | 6/1998 | Knifton et al. | 585/467 |
| 5,777,187 | 7/1998 | Knifton et al. | 585/449 |
| 5,847,254 | 12/1998 | Knifton et al. | 585/463 |

FOREIGN PATENT DOCUMENTS

| | | |
|---|---|---|
| 0 160 144 | 11/1985 | European Pat. Off. |
| 0 353 813 | 2/1990 | European Pat. Off. |
| 0 466 558A1 | 1/1992 | European Pat. Off. |
| WO93/00317 | 1/1993 | WIPO |

OTHER PUBLICATIONS

Almeida, J.L.G. de, M. Dufaux, Y.B. Taarit and C. Naccache, Effect of pore size and aluminum content on the production of linear alkylbenzenes over HY, H–ZSM–5 and H–ZSM–12 zeolites; alkylation of benzene with 1–dodecene, *Applied Catalysis A*: General 114: 141–159, 1994.

Almeida, J.L.G. de, M. Dufaux, Y.B. Taarit and C. Naccache, Linear alkylbenzene, JAOCS 71(7): 675–694, 1994.

Cohen, L.R. Vergara, A. Moreno and J.L. Berna, Influence of 2–phenyl alkane and tetralin content on solubility and viscosity of linear alkylbenzene sulfonate, JAOS 72(1): 115–122, 1995.

Venuto, P.B.L.A. Hamilton P.S. Landis and J.J. Wise, Organic reactions catalyzed by crystaline aluminosukucates I. alkyation reactions, *Journal of catalysis* 4: 81–98, 1966.

Hauan et al., "Why methyl tert–butyl ether production by reactive distillation may yield multiple solutions," *Ind. Eng. Chem. Res.*, 34: 987–994 (1995).

Matouq et al., "Combined process for production of methyl tert–butyl ether from tert–butyl alcohol and methanol," *J. Chem. Engl.* JPN, 27(3): 302–306 (1994).

*Primary Examiner*—Walter D. Griffin
*Attorney, Agent, or Firm*—O'Keefe, Egan & Peterman

[57] ABSTRACT

This invention is directed to a fluorine-containing mordenite catalyst and use thereof in the manufacture of linear alkylbenzene (LAB) by alkylation of benzene with an olefin. The paraffin may have from about 10 to 14 carbons. The fluorine-containing mordenite is prepared typically by treatment with an aqueous hydrogen fluoride solution. The benzene alkylation may be conducted using reactive distillation. This invention is also directed to a process for production of LAB having a high 2-phenyl isomer content by combining LAB product from the fluorine-containing mordenite product from a conventional LAB alkylation catalyst such as hydrogen fluoride.

18 Claims, 4 Drawing Sheets

ALKYLATION OF BENZENE TO FORM LINEAR ALKYLBENZENES USING FLUORINE-CONTAINING MORDENITES

This application is a continuation-in-part application of application Ser. No. 08/598,692, filed Feb. 8, 1996, now U.S. Pat. No. 5,847,254 and of application Ser. No. 08/879,745, filed Jun. 20, 1997, which is a divisional of Ser. No. 08/598,695, filed Feb. 8, 1996, now U.S. Pat. No. 5,770,782, the contents of which are expressly incorporated herein by reference.

BACKGROUND OF THE INVENTION

This invention generally relates to the alkylation of benzene with paraffins using mordenite catalysts.

Linear alkylbenzenes (LAB's) having long chains (typically 10–14 carbons) are commonly used, commercial products. LAB's are commonly sulfonated to thereby produce surfactants.

Typically, LAB's are manufactured commercially using classic Friedal-Crafts chemistry, employing catalysts such as aluminum chloride, or using strong acid catalysts such as hydrogen fluoride, for example, to alkylate benzene with paraffins. While such methods produce high conversions, the selectivity to the 2-phenyl isomer is low, generally being about 30% or less. LAB's with a high percentage of the 2-phenyl isomer are highly desired because such compounds when sulfonated have long "tails" which provide enhanced solubility and detergent properties.

SUMMARY OF THE INVENTION

It has now been recognized that a need exists for a method of LAB production having high substrate olefin conversion, high selectivity to 2-phenyl isomer LAB, and employing a catalyst having long lifetimes and easy handling. This invention provides a solution to one or more of the problems and disadvantages described above.

It has also been found that the catalyst of this invention may be used in combination with an existing aluminum chloride or hydrogen fluoride alkylation facility to afford LAB having a higher 2-phenyl isomer content than would otherwise be available from such plant. Thus, an existing facility may be retrofitted to include one or more reactors containing the fluorine-containing mordenite of this invention. In this manner, a slip stream of reactants may be sent to the mordenite with effluent therefrom being introduced back into the conventional alkylation system. This embodiment has several advantages. For example, the cost of capital is minimized since conventional equipment will already be in place. Also, the retrofitted plant can produce higher 2-phenyl isomer LAB at the discretion of its operator, depending on need. That is, the plant need not produce strictly high 2-phenyl isomer LAB and can instead produce high 2-phenyl isomer at its discretion. In one embodiment, a slip stream of reactant is drawn and sent to one or more reactors containing fluorine-containing mordenite catalyst. The effluent from the fluorine-containing mordenite reactor may then be combined with effluent from the HF or aluminum chloride reactor to provide a product having a higher level of 2-phenyl isomer LAB than would otherwise be present in product from an HF or aluminum chloride reactor.

This invention, in one broad respect, is a process useful for the production of monoalkylated benzene, comprising contacting benzene with an olefin containing from about 8 to about 30 carbons in the presence of fluorine-containing mordenite under conditions such that linear monoalkylated benzene is formed.

In another broad respect, this invention is a process for the production of linear alkylbenzene, comprising:

contacting benzene and an olefin having about 8 to about 30 carbons in the presence of a fluorine-containing mordenite to form a first linear alkylbenzene stream;

contacting benzene and an olefin having about 8 to about 30 carbons in the presence of a conventional linear alkylbenzene alkylation catalyst to form a second linear alkylbenzene stream;

combining the first linear alkylbenzene stream and the second linear alkylbenzene stream form a third linear alkylbenzene stream, as well as the product made from this process.

In another broad respect, this invention is a process useful for the production of linear alkylbenzene, comprising:

combining a product from a conventional linear alkylbenzene alkylation reactor with a product from a linear alkylbenzene alkylation reactor containing fluorine-containing mordenite.

In yet another broad respect, this invention is a process for the production of linear alkylbenzene, comprising:

dehydrogenating a paraffin to form an olefin;

sending a primary feed stream of benzene and the olefin through a conduit to a conventional linear alkylbenzene alkylation reactor;

contacting the primary feed stream in the conventional linear alkylbenzene alkylation reactor with a conventional linear alkylbenzene alkylation catalyst under conditions effective to react the benzene and olefin to form a first linear alkylbenzene product;

withdrawing a portion of the primary feed stream from the conduit and contacting the portion with a fluorine-containing mordenite under conditions effective to react the benzene and olefin to form a second linear alkylbenzene product;

combining the first and second linear alkylbenzene products to form a crude linear alkylbenzene stream;

distilling the crude linear alkylbenzene stream in a first distillation column to separate benzene that did not react and to form a benzene-free linear alkylbenzene stream;

optionally distilling the benzene-free linear alkylbenzene stream in a second distillation column to separate any olefin and to form a linear alkylbenzene stream;

distilling the second olefin free alkylbenzene stream in a third distillation column to provide an overhead of a purified linear alkylbenzene product and removing a bottoms stream containing any heavies.

In another broad respect, this invention is a process useful for the production of monoalkylated benzene, comprising introducing a feed comprising olefin having about 8 to about 30 carbons and benzene into a fluorine-containing mordenite catalyst bed under conditions such that monoalkylated benzene is produced, allowing benzene, olefin, and monoalkylated benzene to descend (fall) into a reboiler from the catalyst bed, removing monoalkylated benzene from the reboiler, and heating the contents of the reboiler such that benzene refluxes to further contact the fluorine-containing mordenite.

In another broad aspect, this invention relates to mordenite useful for alkylating benzene with olefin having a silica to alumina molar ratio of about 10:1 to about 100:1; wherein the mordenite has been treated with an aqueous hydrogen fluoride solution such that the mordenite contains from about 0.1 to about 4 percent fluorine by weight.

In another broad respect, this invention is a method useful for the preparation of fluorine-containing mordenite, comprising contacting a mordenite having a silica to alumina molar ratio in a range from about 10:1 to about 100:1 with an aqueous hydrogen fluoride solution having a concentration of hydrogen fluoride in the range of from about 0.1 to about 10 percent by weight such that the mordenite containing fluorine is produced, collecting the fluorine-containing mordenite by filtration, and drying.

The fluorine treated mordenite catalyst advantageously produces high selectivities to the 2-phenyl isomer in the preparation of LAB, generally producing selectivities of about 70 percent or more. Also, the fluorine treated mordenite enjoys a long lifetime, preferably experiencing only a 25 percent or less decrease in activity after 400 hours on stream. A process operated in accordance with the apparatus depicted in FIGS. 1 and 2 has the advantage that rising benzene from the reboiler continuously cleans the catalyst to thereby increase lifetime of the catalyst. In addition, this invention advantageously produces only low amounts of dialkylated benzene, which is not particularly as useful for detergent manufacture, as well as only low amounts of tetralin derivatives.

Certain terms and phrases have the following meanings as used herein.

"Meq/g" means milliequivalents of titratable acid per gram of catalyst, which is a unit used to describe acidity of the catalysts. Acidity is generally determined by titration with a base, as by adding excessive base, such as sodium hydroxide, to the catalyst and then back titrating the catalyst.

"Conv." and "Conversion" mean the mole percentage of a given reactant converted to product. Generally, olefin conversion is about 95 percent or more in the practice of this invention.

"Sel." and "Selectivity" mean the mole percentage of a particular component in the product. Generally, selectivity to the 2-phenyl isomer is about 70 or more in the practice of this invention.

The mordenite catalyst of the present invention is useful as a catalyst in the production of LAB's in accordance with the process of manufacturing LAB's of this invention. LAB is useful as starting material to produce sulfonated LAB, which itself is useful as a surfactant.

DETAILED DESCRIPTION OF THE INVENTION

Catalyst Preparation and Properties

Figure 1:
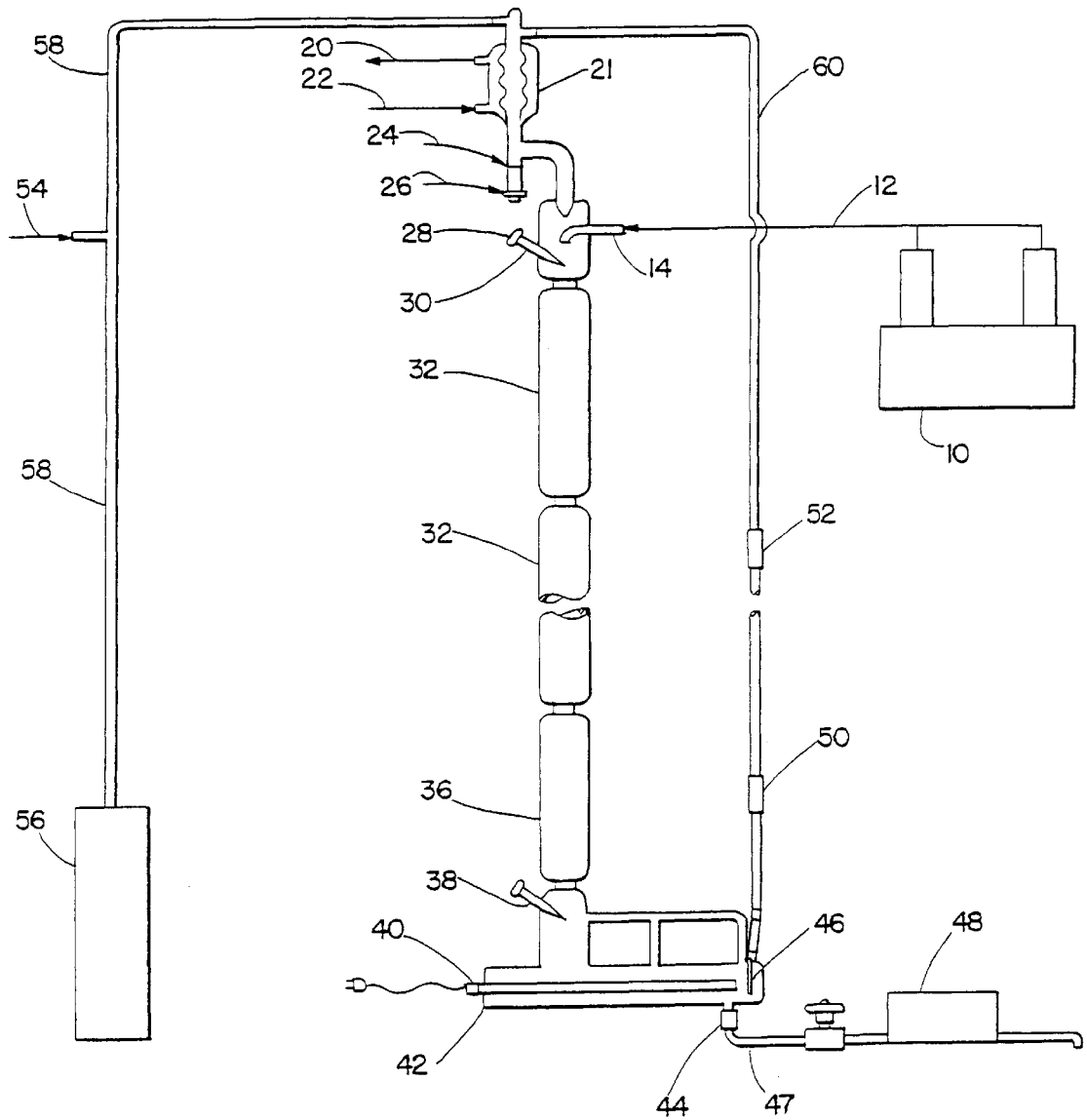
FIG. 1 shows a representation of a first continuous reactive distillation column employed in the practice of this invention.

The catalyst of this invention is a fluorine-containing mordenite. Mordenite is a type of zeolite. The catalyst of this invention is prepared from hydrogen mordenite (typically having 0.1 percent or less of sodium) having a silica-alumina molar ratio of from about 10:1 to about 100:1. More typically, the starting mordenite has a silica/alumina molar ratio of from about 10:1 to about 50:1. The starting hydrogen mordenite, which is commonly available commercially, is treated with an aqueous solution of hydrogen fluoride ("HF") to produce the active, long-life and highly selective catalyst of the invention. In the course of such HF treatment, as well as during subsequent calcination of said HF-treated mordenite, the silica/alumina molar ratio typically increases. The finished catalysts of this invention show a fluorine content of from about 0.1 to about 4 percent by weight, more typically about 1 percent.

While not wishing to be bound by theory, it is believed that the HF reacts with sites where—Si—O—Al— linkages occur such that the linkage is broken with fluorine becoming bonded to the Al such that —Si—OH and F—Al— groups form. This is believed to decrease the total Bronsted acid sites and increase the strength of the remaining acid sites in the mordenite and is believed to stabilize the acidity of the mordenite such that the mechanisms which degrade performance during LAB production, such as coke build-up, are retarded.

The aqueous solution used to treat the mordenite may contain a range of HF concentrations. Generally, the HF concentration is a minimum of about 0.1 percent by weight. Below such minimum concentration, the effect of the fluorine treatment significantly decreases, resulting in the undesirable need for repeated treatments. Generally, the HF concentration on the upper end is about 10 percent by weight or less. Above a concentration of about 10 percent by weight, the HF is so concentrated that it is difficult to prevent HF from destroying the crystallinity of the mordenite, thereby detrimentally affecting its efficacy as a catalyst for LAB production.

The aqueous HF solution may be prepared by diluting commercially available 48% HF solutions to the desired concentration. Alternatively, HF can be sparged into water to provide an aqueous HF solution.

Typically, the treatment is carried out by adding mordenite powder or pellets to a stirred aqueous HF solution at a temperature of from about 0° C. to about 50° C. The stirring and contacting is continued for a time sufficient to achieve the desired level of fluorine in the mordenite. This time may vary depending on factors such as HF concentration, amount of HF solution relative to the amount of mordenite being treated, speed of agitation is employed, and temperature. After treatment, the mordenite can be recovered by filtration, and then dried. It is also possible to impregnate the mordenite to incipient wetness with a given HF solution, as well as to treat the mordenite with gaseous hydrogen fluoride. Preferably said fluoride-treated mordenite would be calcined in air prior to use in alkylation service. The preferred calcination temperature would be in the range from about 400° C. to about 600° C. Alternative mordenite fluorinating agents to hydrofluoric acid and hydrogen fluoride include ammonium fluoride, fluorided silicon compounds and fluorided hydrocarbons.

The HF-treated mordenite of this invention generally has about 0.1 percent by weight or more of fluorine based on the total weight of the mordenite. Typically, the fluorine-containing mordenite contains about 4 percent by weight or less fluorine. The fluorine-containing mordenite most typically contains about 1 percent by weight of fluorine.

The mordenite can be used in the practice of this invention as a powder, in pellet form, as granules, or as extrudates. The mordenite can be formed into pellets or extrudates using binders well known to those of skill in the art, such as alumina, silica or mixtures thereof.

Reactants for LAB Production

In the practice of this invention, benzene is alkylated with olefin to form LAB. These reactants can be handled and purified as is generally performed by those of skill in the art. In this regard, it is preferred that the reactants are water and alcohol free. The olefins employed in the practice of this invention have from about 8 to about 30 carbons, preferably from about 10 to about 14 carbons, such as is available commercially or produced as dehydrogenated paraffin feed stocks. It is preferred that the olefin be monounsaturated. It is most preferred that the olefin be an alpha-olefin containing a terminal ethylenic unit.

Commonly, said olefins would be available in a paraffini media of the same carbon range. Olefins in the 10 to 14 carbon number range would typically be available from $C_{-10}$ to $C_{-14}$ paraffin dehydrogenation in a $C_{-10}$ to $C_{-14}$ paraffin mixture having an olefin content of 5 to 20%. Often, the olefin content of said paraffin-olefin mixture would be 8 to 10 weight %.

The 2-phenyl isomer of the LAB produced in accordance with this invention is of formula:

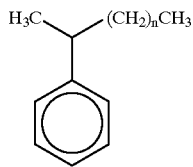

wherein n is from about 5 to about 17 and preferably from about 7 to about 11.

Process Conditions, Procedures, and Apparatus

The process of this invention can be carried out using the continuous reactive distillation column depicted in FIG. 1. In FIG. 1, a feed mixture of benzene and olefin, generally at a benzene-to-olefin molar ratio range of about 1:1 to 100:1 flows from feed pump 10 to feed inlet 14 via line 12. The feed mixture falls to packed mordenite catalyst bed 32 where alkylation in the presence of the fluorine-containing mordenite occurs. Alternatively, while not depicted in FIG. 1, the benzene and olefin can be introduced separately into the bed with mixing occurring in the bed, or the reactants can be mixed via an in-line mixer prior to introducing the reactants into the catalyst bed, or the reactants can be injected separately above the bed with mixing affected by use of standard packing above the bed, or the reactants can be sparged into the chamber above the bed. The catalyst bed 32 depicted in FIG. 1 for laboratory scale may be made of two lengths of 1.1 inch internal diameter tubing, the lengths being 9.5 inches and 22 inches. In the catalyst bed 32, the falling feed mixture also contacts rising vapors of unreacted benzene which has been heated to reflux in reboiler 42 by heater 40. Such rising vapors pass over thermocouple 38 which monitors temperature to provide feedback to heater 40. The rising vapors of benzene and/or olefin also pass through standard packing 36 (e.g., 7.5 inches of goodloe packing). The rising vapors heat thermocouple 30 which connects to bottoms temperature controller 28 which activates heater 40 when temperature drops below a set level.

Prior to startup, the system may be flushed with nitrogen which enters via line 54 and which flows through line 58. After startup, a nitrogen blanket is maintained over the system. Also prior to startup and during nitrogen flush, it may be desirable to heat catalyst bed 32 so as to drive off water from the fluorine-containing mordenite.

Residual water from the feed mixture or which otherwise enters the system is collected in water trap 24 upon being liquefied at condenser 21 (along with benzene vapor). If the feed is very dry (free of water) the water trap 24 may not be needed. Removing water leads to longer catalyst lifetime. Hence, the water trap 24 is optional. The same applies to FIG. 2. Condenser 21 is cooled via coolant such as water entering condenser 21 via port 22 and exiting via port 20. As needed, water in water trap 24 may be drained by opening drain valve 26.

As needed, when LAB content in reboiler 42 rises to a desired level, the bottoms LAB product may be removed from the system via line 47, using either gravity or bottoms pump 48 to withdraw the product. When product is so withdrawn, valve 44 is opened.

In FIG. 1, dip tube 46, which is optional, is employed to slightly increase the pressure in reboiler 42 to thereby raise the boiling point of benzene a degree or two. Likewise, a pressure generator 56 may be optionally employed to raise the pressure of the system. Other standard pressure increasing devices can be employed. Pressure cam thus be increased in the system such that the boiling point of benzene increases up to about 200° C.

In FIG. 1, control mechanisms for heat shutoff 50 and pump shutoff 52 are depicted which serve to shut off heat and pump if the liquids level in the system rises to such levels. These control mechanisms are optional and may be included so that the catalyst bed does not come into contact with the bottoms of the reboiler. Line 60 connects pump shutoff 52 to the system above condenser 21.

Figure 2:
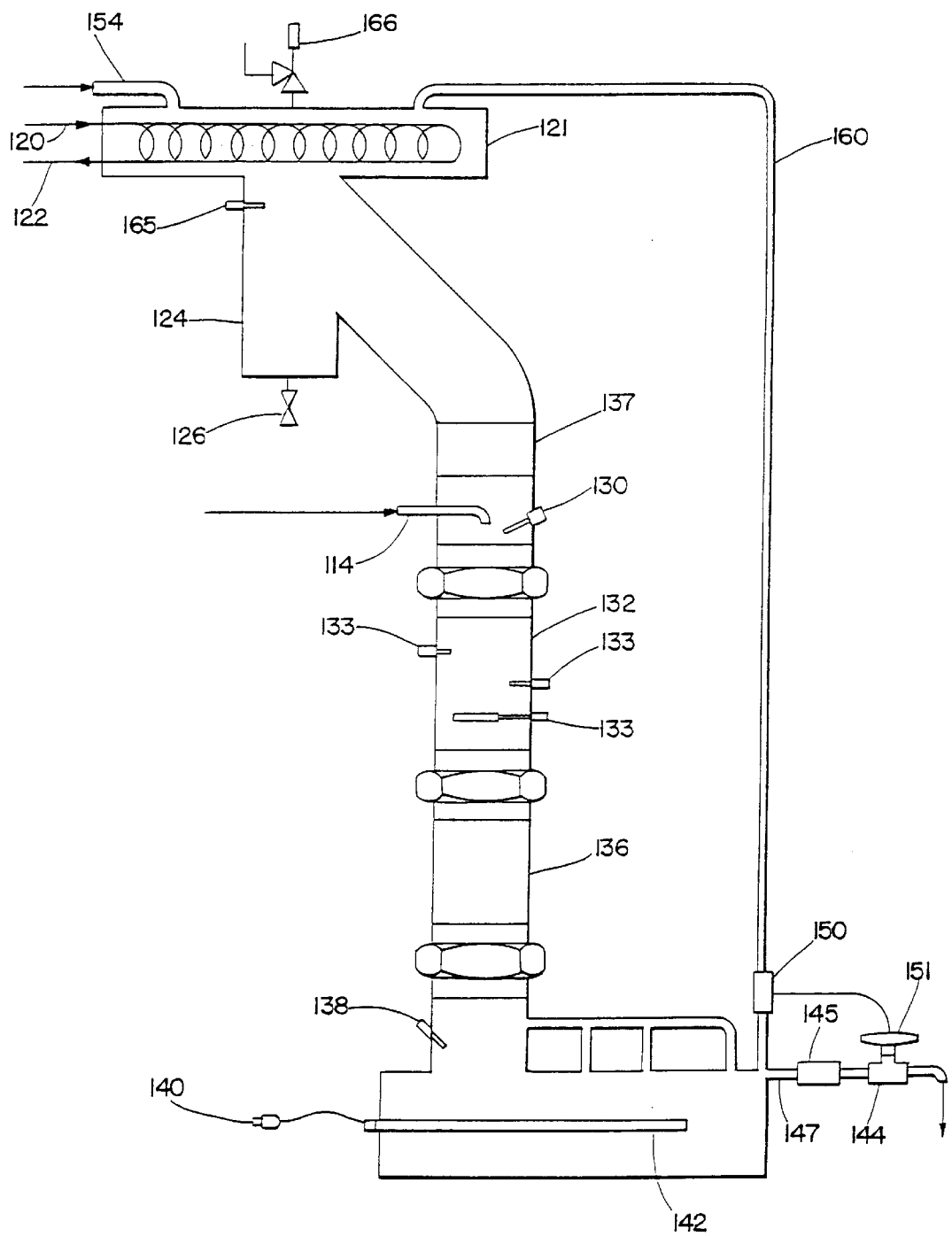
FIG. 2 shows a representation of a second continuous reactive distillation column employed in the practice of this invention.

In the practice of this invention in the alkylation of benzene, a wide variety of process conditions can be employed. In this regard, the temperature in the catalyst bed may vary depending on reactants, rate of introduction into the catalyst bed, size of the bed, and so forth. Generally, the bed is maintained at the reflux temperature of benzene depending on pressure. Typically, the temperature of the catalyst bed is above about 70° C., and most likely about 78° C. or more in order to have reasonable reaction rates, and about 200° C. or less to avoid degradation of reactants and products and to avoid deactivation of the catalyst by coke build-up. Preferably, the temperature is in the range from about 80° C. to about 140° C. The process may be operated at a variety of pressures during the contacting step, with pressures of about atmospheric most typically being employed. When the process is operated using a system as depicted in FIGS. 1 and 2, the reboiler temperature is maintained such that benzene and olefin vaporize, the temperature varying depending on olefin, and generally being from about 80° C. to about 250° C. for olefins having 10 to 14 carbons. The composition of the reboiler will vary over time, but is generally set initially to have a benzene olefin ratio of about 5:1, with this ratio being maintained during the practice of this invention. The rate of introduction of feed into the catalyst bed may vary, and is generally at a liquid hourly space velocity ("LHSV") of about 0.05 hr$^{-1}$ to about 10 hr$^{-1}$, more typically from about 0.05 hr$^{-1}$ to about 1 hr$^{-1}$. The mole ratio of benzene to olefin introduced into the catalyst bed is generally from about 1:1 to about 100:1. In commercial benzene alkylation operations, it is common to run at mole ratios of from about 2:1 to about 20:1, which can suitably be employed in the practice of this invention, and to charge said olefins as an paraffin-olefin mixture comprising 5% to 20% olefin content. Said paraffin-olefin mixtures are normally generated commercially through dehydrogenation of the corresponding paraffin starting material over a noble metal catalyst.

Another continuous reactive distillation apparatus is depicted in FIG. 2. In FIG. 2, the feed mixture enters the reactor via feed inlet 114. The feed mixture falls through the column into catalyst bed 132, wherein alkylation to form LAB occurs. A thermowell 133 monitors the temperature of said catalyst bed 132. The catalyst bed 132 may be optionally heated externally and is contained within 1¼ inch stainless steel tubing. Goodloe packing is positioned at packing 136 and 137. LAB product, as well as unreacted benzene and olefin, fall through packing 136 into reboiler 142. In reboiler 142, electric heater 140 heats the contents of reboiler 142 such that heated vapors of benzene and olefin rise from the reboiler 142 to at least reach catalyst bed 132. As needed, the bottoms LAB product may be removed from reboiler 142 by opening bottoms valve 144 after passing through line 147 and filter 145. Residual water from the feed mixture, or which otherwise enters the system, may be condensed at condenser 121 which is cooled with coolant via outlet line 122 and inlet line 120. The condensed water falls to water trap 124, which can be drained as needed by opening drain valve 126. Temperature in the system is monitored via thermocouples 138, 130, and 165. The system includes pressure release valve 166. A nitrogen blanket over the system is maintained by introduction of nitrogen gas via inlet line 154. Level control activator 150 activates bottoms level control valve 151 to open when the liquids level in the reboiler rises to the level control activator 150. Line 160 connects level control activator 150 to the system above condenser 121.

While the systems depicted in FIG. 1 and FIG. 2 show single catalyst bed systems, it may be appreciated that multi-catalyst bed reactors are within the scope of this invention, as well as multiple ports for inlet feeds, water traps, product removal lines, and so forth. Moreover, the process may be run in batch mode, or in other continuous processes using plugflow designs, trickle bed designs, and fluidized bed designs.

It is believed that as average molecular weight of olefins increases, particularly when the average number of carbons exceed 14, the selectivity and conversion to LAB, especially LAB with the 2-isomer, may incrementally decrease. If desired, the product of the alkylation using HF-treated mordenite may be sent to a second, finishing catalyst bed to improve yield. This procedure is optional and is believed to be dependent on the needs and desires of the end user. An example of such a second catalyst is HF-treated clay such as montmorillonite clay having about 0.5% fluoride. Such a catalyst may also serve to lower the bromine number below about 0.1, depending on conditions.

Variable 2-phenyl Isomer Content of Product Using the Mordenite of this Invention in Combination with Conventional LAB Alkylation The fluorine-containing mordenite of this invention generally produces LAB having high 2-phenyl isomer content, such as higher than about 70%. Currently, LAB purchasers who make detergents would prefer to use LAB having a 2-phenyl isomer content in the range from about 30 to about 40 percent, but this level is not available in the marketplace. Conventional LAB alkylation technology do not achieve these higher 2-phenyl isomer levels. HF, which is currently the most widely used catalyst for production of LAB on a commercial scale, produces about 16–18 percent of the 2-phenyl isomer in the product stream from the reactor. Aluminum chloride, in contrast, produces about 26–28 percent of the 2-phenyl isomer. The present inventors recognized that a need exists for a process which produces a 2-phenyl isomer product in the desired range.

It has now been found that the mordenite of this invention can be used in combination with conventional LAB alkylation catalysts, such as HF and aluminum chloride alkylation catalysts. This may be affected by withdrawing a slip stream of reactant that is being sent to the conventional LAB reactor, and directing the slip stream to the mordenite reactor. Since conventional LAB catalysts produce product having a 2-phenyl isomer content much less than that from mordenite of this invention, combining the products from each catalyst results in a product having a higher 2-phenyl isomer content than that from the conventional LAB alkylation catalyst. For example, while the catalyst of this invention typically produces a 2-phenyl isomer content of 70% or more, a typical HF process produces about 16–18% of the 2-phenyl isomer. By combining effluent from each catalyst at given proportions, the resulting mixture will have any desired 2-phenyl isomer content in the range between the 2-phenyl isomer contents of the HF catalyst product and the mordenite catalyst product. Thus, the levels of 2-phenyl isomer may be adjusted by the amount of reactants sent to the mordenite catalyst and/or by storing 2-phenyl isomer product from the mordenite catalyst for later mixing with the product of from the conventional LAB alkylation catalyst to thereby achieve any desired level of 2-phenyl isomer content in the final product. An advantage of this invention pertains to the ability to retrofit an existing, conventional LAB system with a reactor containing fluorine-treated mordenite of this invention. This enables existing users of the conventional LAB technology to augment their existing facilities without interrupting their production. This provides a considerable cost advantage to the producer.

The conventional LAB catalysts used most frequently are HF alkylation reactors and aluminum chloride alkylation catalysts. Other alkylation catalysts include various zeolites, alumina-silica, various clays, as well as other catalysts.

Figure 3:
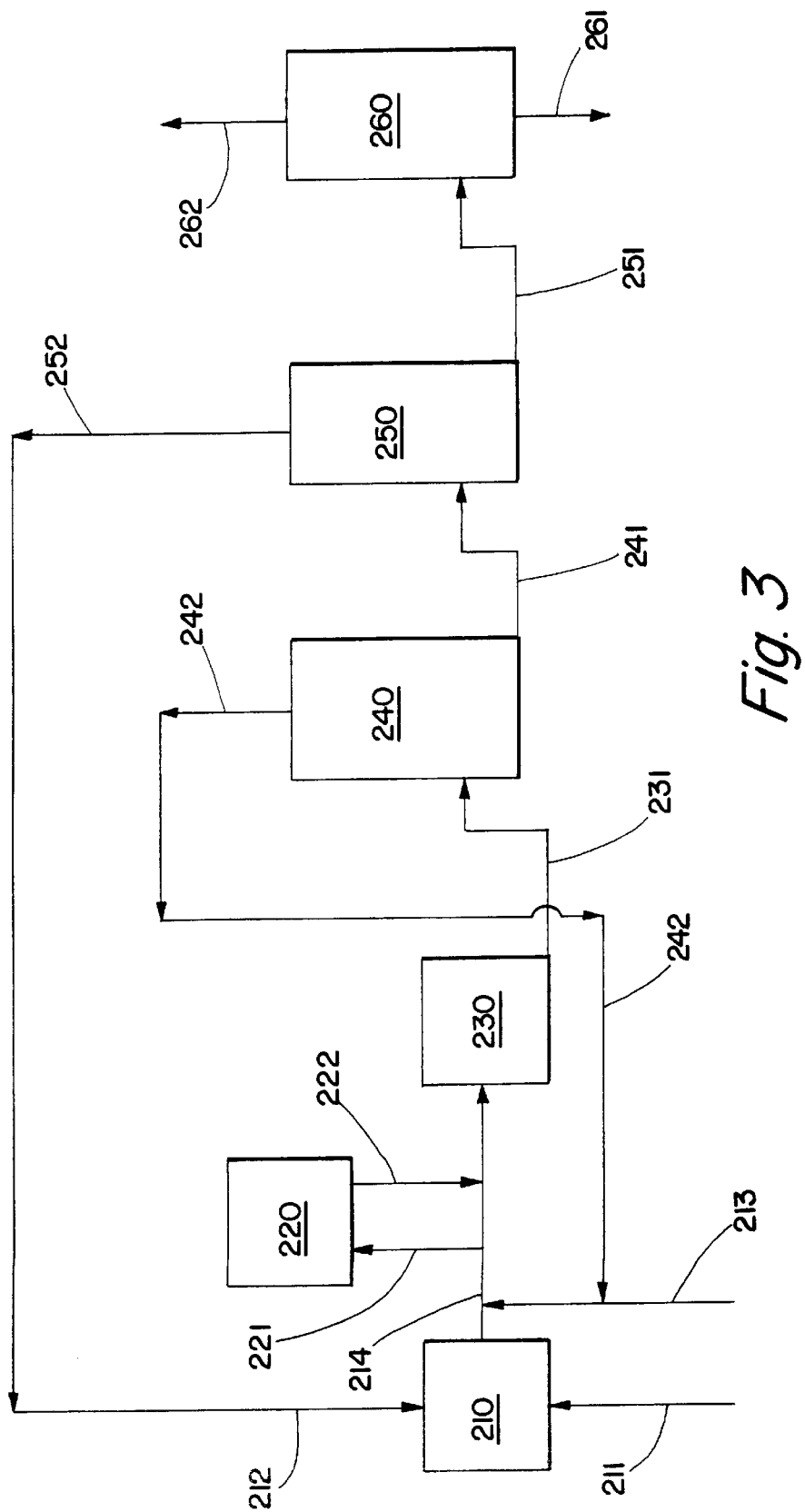
FIG. 3 shows a representative process scheme for one embodiment of this invention where a conventional LAB alkylation reactor is shown in combination with a fluorine-containing mordenite reactor of this invention wherein a slip stream of reactant to the conventional reactor is sent to the mordenite reactor and wherein the flow of high 2-phenyl isomer LAB from the mordenite reactor may be adjusted to vary the 2-phenyl isomer LAB content of the effluent from the conventional LAB alkylation reactor.

FIG. 3 depicts a representative, non-limiting scheme for practice of this invention wherein the fluorine-treated mordenite is used in combination with a HF alkylation reactor to afford LAB having high 2-phenyl isomer contents relative to that produced from the HF reactor alone. The scheme of FIG. 3 is shown in the context of LAB alkylation based on a feed from a paraffin dehydrogenation facility. Prior to this invention, the plant depicted in FIG. 3 would be operated conventionally without use of mordenite reactor 220.

Thus, in conventional operation, fresh paraffin is fed to conventional dehydrogenation apparatus 210 via line 211, with recycled paraffin being introduced from the paraffin column 250 via line 252. Dehydrogenated paraffin from the dehydrogenation apparatus 210 is then pumped into a conventional alkylation reactor 230 containing conventional LAB catalyst, such as HF, via conduit 214. The dehydrogenated paraffin feed may of course be supplied from any provider. The source of dehydrogenated paraffin (olefin) is not critical to the practice of this invention. LAB product from alkylation unit 230 may thereafter be purified by a series of distillation towers.

In this regard, alkylation effluent is delivered to a benzene column 240 by way of line 231. It should be appreciated that the alkylation product may be sent offsite for purification. Further, the particular purification scheme used is not critical to the practice of this invention, but is depicted in FIG. 3 as representative of a typical commercial operation. In FIG. 3, unreacted benzene is distilled off from the crude LAB product. Benzene is then recycled to the alkylation reactor 230. The benzene-free LAB crude product from the benzene column 240 is pumped through line 241 to olefin column 250 where any olefin present is distilled off, with the distilled olefin being recycled to paraffin dehydrogenation unit 210 via line 252. Olefin-free crude LAB alkylate from the olefin column 250 is transported to a refining column 260 where purified LAB is distilled and removed via line 262. Heavies (e.g., dialkylates and olefin derivatives) are withdrawn from refining column 260 via conduit 261.

In the practice of this invention, a fluorine-treated mordenite containing reactor 220 is used in conjunction with the conventional alkylation reactor 230. In the embodiment of this invention depicted in FIG. 3, a slip stream of benzene/dehydrogenated paraffin feed is taken from line 214 and pumped through mordenite reactor 220 where high 2-phenyl isomer production is achieved. LAB product from reactor 220, high in 2-phenyl isomer, is then introduced back into line 214 via line 222. Alternatively mordenite reactor 220 may be fed benzene and dehydrogenated paraffin (olefin) directly, rather than by way of a slip stream from line 221. In addition, effluent from reactor 220 may, in the alternative if no unreacted olefin is present, be sent directly to benzene column 240, for later combination with conventional alkylation reactor 230 product or transported and tied into conduit 231, which feeds benzene column 240. It should be appreciated that columns 240, 250, and 260 may be maintained at conditions (e.g., pressure and temperature) well known to those of skill in the art and may be packed with conventional materials if desired.

Figure 4:
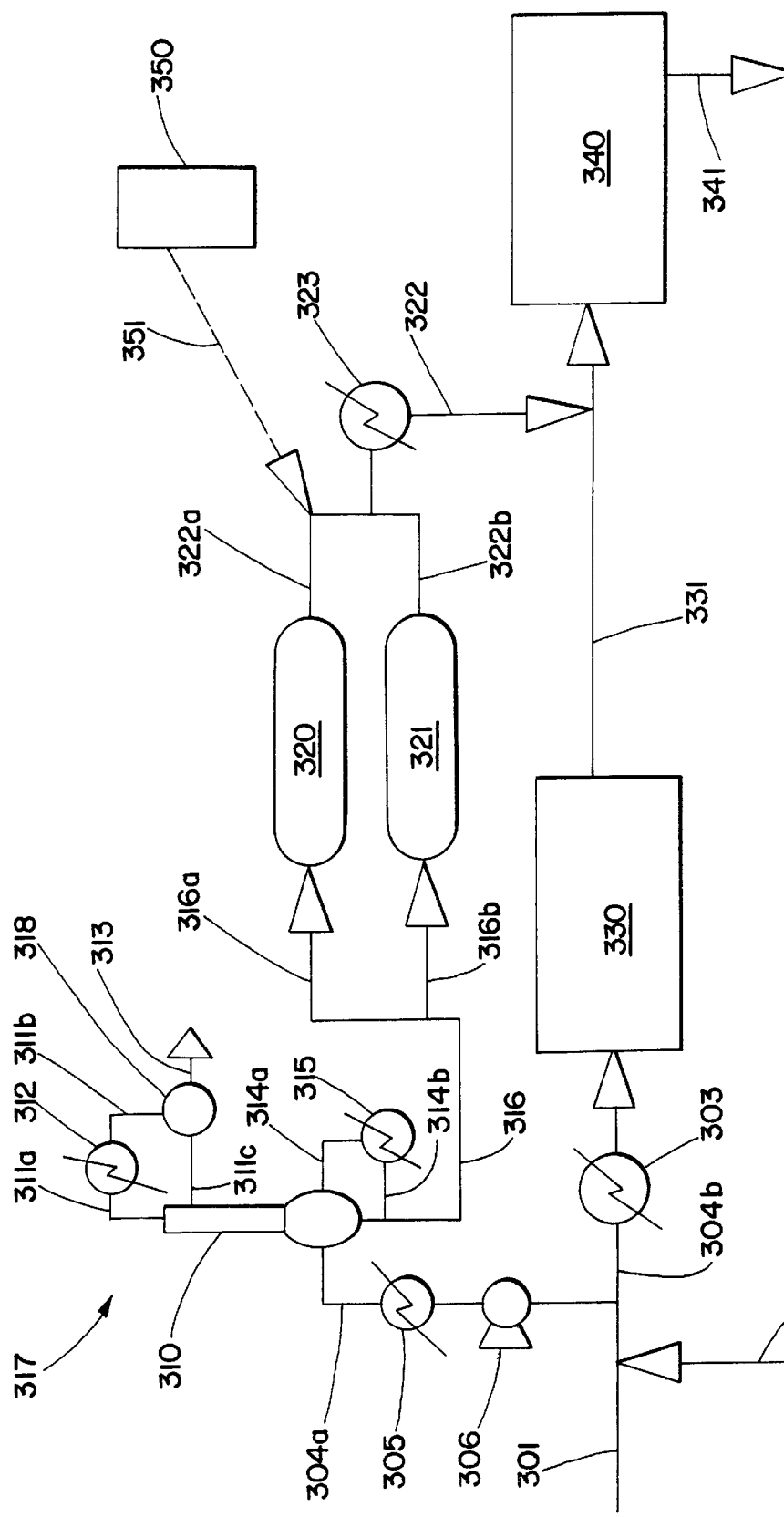
FIG. 4 shows another representative process scheme for one embodiment of this invention where a first conventional LAB alkylation reactor is shown in combination with a fluorine-containing mordenite reactors of this invention wherein a slip stream of reactant to the conventional reactor is sent to one or both of a pair of mordenite reactor and wherein the effluent from the first LAB alkylation reactor and the effluent from the one or both mordenite reactors are combined and flowed into a second conventional LAB alkylation reactor.

FIG. 4 depicts an alternative configuration to that shown in FIG. 3. In FIG. 4, dual mordenite beds 320, 321 are used in conjunction with conventional alkylation reactors 330, 340. Conveniently, one of the mordenite reactors may be in operation while the other reactor is down for catalyst regeneration. For example, during operation, olefin feed (dehydrogenated paraffin) is supplied via line 301, with benzene or other aromatic feed stock being provided via line 302. The admixed reactants may flow to standard alkylation reactor 330 via line 304b after passing through heat exchanger 303. A portion of the mixed stream may be withdrawn via line 304a for supply to the mordenite reactor. The extent of the mixed feed stream being withdrawn may be varied depending on the desired level of 2-phenyl isomer in the final product. In another embodiment, the product from the reactor containing mordenite 320, 321 may be fed to the first alkylation reactor 330, particularly if the second alkylation reactor 34 is not employed in the process.

The slip stream reactants may optionally be sent to dewatering unit 317 by application of pump 306 after passing through heat exchanger 305. In the dewatering unit 317, water is distilled from the reactants in dewatering tower 310. Rising vapor exits via line 311a and passes through heat exchanger 312 wherein condensation occurs. Effluent from heat exchanger 312 is advanced to water trap 318 via line 311b. Water is removed from water trap 318 via line 313, with the bottom organic layer being returned to the dewatering tower 310. Dewatered reactants may be removed via line 316 and conveyed to either line 316a or line 316b. Some of the dewatered reactant may be withdrawn by conduit 314b, sent through heat exchanger 315 and returned to the tower 310 via line 314a. In this regard, heat exchanger 315 may serve as a reboiler.

After reaction in either reactor 320 or 321, LAB product is sent to lines 322 and 331 from either line 322a or 322b after passing through heat exchanger 323. When desired, one of the catalyst beds may be regenerated, as by calcination for example, through use of regeneration heater 350, which may be connected to the reactor of choice by dotted line 351 through valving and hardware that are not shown. The reactors 320 and 321 may optionally be run simultaneously. The reactors 320 and 321 may be loaded with mordenite catalyst in any fashion, as would be apparent to one of skill in the art. Typically, a plugged flow arrangement is used. The amount of catalyst employed may vary depending on a variety of considerations such as type and flow rate of reactants, temperature and other variables. The combined effluents from conventional reactor 330 and mordenite reactors 320 or 321 may be fed to a second conventional reactor 340, or optionally may be sent to a purification section directly if no unreacted paraffin is present (the conventional reactor serves to complete reaction of any paraffin that is not converted in the mordenite reactors 320, 321). In FIG. 4, effluent from the second conventional alkylation reactor is advanced to a purification section. The second alkylation reactor may be used to react unreacted feed stock from reactors 330, 320 and 321 to thereby reduce recycle loads.

It should be appreciated that a wide variety of configurations are contemplated, and the figures should not be construed as limiting this invention or claims hereto. Additional reactors and other equipment may, for example, be used.

The following examples are illustrative of the present invention and are not intended to be construed as limiting the scope of the invention or the claims. Unless otherwise indicated, all percentages are by weight. In the examples, all reactants were commercial grades and used as received. The apparatus depicted in FIG. 1 was employed for examples 2–4. The apparatus depicted in FIG. 1 was used for example 5.

It may be noted that example 2 illustrates LAB production from paraffin dehydrogenate using the fluoride-treated mordenite catalyst of example B, where good catalyst life (250+ hrs) is achieved without catalyst regeneration, while maintaining a 2-phenyl LAB selectivity of >70% and high LAB productivity without significant loss of fluoride. Comparative example 1, on the other hand, using untreated mordenite, with no fluoride added, shows a rapid decline in LAB production. In addition, examples 3 and 4 illustrate LAB production using a 5:1 molar benzene/$C_{10}$–$C_{14}$ olefin feed mix and the fluoride-treated mordenite catalysts of Example B when operating at different LHSV's in the range of 0.2–0.4 $hr^{-1}$. Catalyst life may exceed 500 hours. Example 5 illustrates LAB production with the fluoride-treated mordenite catalyst where the alkylation is conducted at higher temperatures and under pressure. Examples 6–8 illustrate the performance of three HF-treated mordenite catalysts with different fluoride loadings. Example 9 shows how virtually no alkylation activity is observed with a highly-fluorinated mordenite.

EXAMPLE A

This example illustrates the preparation of a hydrogen fluoride-modified mordenite.

To 30 g of acidified mordenite (LZM-8, $SiO_2/Al_2O_3$ ratio 17; $Na_2O$ wt % 0.02, surface area 517 $m^2/g$, powder, from Union Carbide Corp.) was added 600 ml of 0.4% hydrofluoric acid solution, at room temperature. After 5 hours the solid zeolite was removed by filtration, washed with distilled water, dried at 120° C. overnight, and calcined at 538° C.

EXAMPLE B

The example illustrates the preparation of a hydrogen fluoride-modified mordenite.

To 500 g of acidified, dealuminized, mordenite (CBV-20A from PQ Corp.; $SiO_2/Al_2O_3$ molar ratio 20; $Na_2O$, 0.02 wt %; surface area 550 $m^2/g$, 1/16" diameter, extrudates, that had been calcined at 538° C., overnight) was added a solution of 33 ml of 48% HF solution in 1633 ml of distilled water, the mix was cooled in ice, stirred on a rotary evaporator overnight, then filtered to recover the extruded solids. The extrudates were further washed with distilled water, dried in vacuo at 100° C., and then calcined at 538° C., overnight.

Analyses of the treated mordenite showed:

| | |
|---|---|
| F: | 1.2% |
| Acidity: | 0.49 meq/g |

EXAMPLE 1

This example illustrates the preparation of linear alkylbenzenes using a hydrogen fluoride-modified mordenite catalyst.

To a 500 ml flask, fitted with condenser and Dean Stark Trap was added 100 ml of benzene (reagent grade) plus 10 g of hydrogen fluoride-modified mordenite zeolite, prepared by the method of Example A. The mix was refluxed for 15–20 minutes to remove small amounts of moisture, then a combination of benzene (50 ml) plus 1-dodecene (10 g) was injected into the flask and the solution allowed to reflux for 3 hours.

Upon cooling, the modified mordenite catalyst was removed by filtration, the filtrate liquid flashed to remove unreacted benzene, and the bottoms liquid analyzed by gas chromatography.

Typical analytical data are summarized in Table 1.

TABLE 1

| DODECENE CONV. (%) | LAB ISOMER DISTRIBUTION (%) | | | | | HEAVIES (%) | LINEAR LAB (LLAB) (%) |
|---|---|---|---|---|---|---|---|
| | 2-Ph | 3-Ph | 4-Ph | 5-Ph | 6-Ph | | |
| 99.7 | 79.9 | 16.6 | 0.8 | 1.3 | 1.3 | 0.2 | 95.9 |

EXAMPLE 2

This example illustrates the preparation of linear alkylbenzenes from paraffin dehydrogenate using a hydrogen fluoride-treated mordenite catalyst.

In the example, benzene was alkylated with a sample of $C_{10}$–$C_{14}$ paraffin dehydrogenate containing about 8.5% $C_{10}$–$C_{14}$ olefins. Alkylation was conducted in a process unit as shown in FIG. 1.

Alkylation was conducted by first charging 500 ml of a benzene/paraffin dehydrogenate mix (10:1 molar ratio, benzene/$C_{10}$–$C_{14}$ olefin) to the reboiler and 250 cc of the HF-treated mordenite of example B to the 1.1" i.d. reaction zone. The mordenite was held in place using Goodloe packing. The reboiler liquid was then heated to reflux and a benzene plus $C_{10}$–$C_{14}$ paraffin dehydrogenate mix (10:1 molar ratio, benzene/$C_{10}$–$C_{14}$ olefin) continuously introduced into the unit above the catalyst column at the rate of 100 cc/hr. (LHSV=0.4 $hr^{-1}$).

Under steady state, reflux, conditions liquid product was continuously withdrawn from the reboiler and water continuously taken off from the water trap. The crude liquid product was periodically analyzed by gas chromatography. The reboiler temperature was typically in the controlled range of 97–122° C. The column head temperature variability was 78–83° C. A summary of the analytical results may be found in Table 2.

After 253 hours on stream, the recovered HF-treated mordenite catalyst showed by analysis:

| | |
|---|---|
| F: | 1.1% |
| Acidity: | 0.29 meq/g |
| $H_2O$: | 0.3% |

TABLE 2

| Time on Stream (Hrs) | Sample | Alkylate Conc. (%) | 2-Phenyl Sel. (%) | $C_6H_6$ Conc. (%) |
|---|---|---|---|---|
| 0 | 0 | 1.4 | | 32.3 |
| 2 | 1 | 3.4 | | 19.7 |
| 4 | 2 | 5.8 | 74.9 | 16.6 |
| 6 | 3 | 6.6 | 75.8 | 25.2 |
| 32 | 4 | 7.9 | 80.7 | 27.0 |
| 56 | 5 | 7.8 | 82.7 | 27.0 |
| 69 | 6 | 7.3 | 81.4 | 27.4 |
| 94 | 7 | 6.5 | 82.0 | 27.8 |
| 118 | 8 | 6.0 | 78.4 | 27.7 |
| 142 | 9 | 5.9 | 81.3 | 26.9 |
| 166 | 10 | 5.4 | 81.5 | 27.3 |
| 207 | 11 | 5.3 | 81.3 | 26.1 |
| 229 | 12 | 5.1 | 81.1 | 27.4 |
| 253 | 13 | 4.9 | 81.4 | 28.1 |

Comparative Example 1

This example illustrates the preparation of linear alkylbenzene from paraffin dehydrogenate using an untreated mordenite catalyst.

Following the procedures of Example 9, the alkylation unit was charged with 250 cc of untreated, calcined, mordenite, (the starting mordenite of Example B), and the liquid feed comprised benzene plus $C_{10}$–$C_{14}$ paraffin dehydrogenate mix in a 10:1 molar ratio of benzene/$C_{10}$–$C_{14}$ olefin.

Typical results are summarized in Table 3.

The recovered mordenite showed by analysis:

| | |
|---|---|
| Acidity: | 0.29 meq/g |
| $H_2O$: | 2.1% |

TABLE 3

| Time on Stream (Hrs) | Sample | Alkylate Conc. (%) | 2-Phenyl Sel. (%) | $C_6H_6$ Conc. (%) |
|---|---|---|---|---|
| 0 | 0 | | | 11.2 |
| 2 | 1 | 6.50 | | 9.9 |
| 4 | 2 | 7.16 | 73.2 | 17.1 |
| 6 | 3 | 7.09 | 73.1 | 26.4 |
| 22 | 4 | 8.61 | 73.9 | 26.6 |
| 31 | 5 | 10.49 | 67.4 | 15.8 |
| 46 | 6 | 7.39 | 75.0 | 27.7 |
| 70 | 7 | 6.39 | 75.1 | 28.5 |
| 93 | 8 | 6.08 | 73.6 | 23.0 |
| 144 | 9 | 5.21 | 73.6 | 15.8 |
| 157 | 10 | 4.40 | 73.9 | 26.2 |
| 180 | 11 | 3.06 | 69.6 | 27.1 |
| 204 | 12 | 1.32 | | 19.5 |
| 228 | 13 | 1.32 | | 33.3 |

EXAMPLE 3

This example also illustrates the preparation of linear alkylbenzene from paraffin dehydrogenate using a hydrogen fluoride-treated mordenite catalyst.

Following the procedures of Example 2, the alkylation unit was charged with 250 cc of the HF-treated mordenite of Example B, and the liquid feed comprised a benzene plus $C_{10}$–$C_{14}$ paraffin dehydrogenate mix in a 5:1 molar ratio of benzene/$C_{10}$–$C_{14}$ olefin, the reboiler temperature was typically in the range of 122–188° C., the column head temperature 78–83° C. Typical analytical results are summarized in Table 4.

After 503 hours on stream, the recovered HF-treated mordenite catalyst showed on analysis:

| F: | 1.0% |
|---|---|
| Acidity: | 0.35 meq/g |
| $H_2O$: | 0.1% |

TABLE 4

| Time on Stream (Hrs) | Sample | Alkylate Conc. (%) | 2-Phenyl Sel. (%) | $C_6H_6$ Conc. (%) | Corrected[a] Alkylate Conc. (%) |
|---|---|---|---|---|---|
| 0 | 0 | 1.0 | | 8.9 | 1.1 |
| 2 | 1 | 3.5 | 61.8 | 0.3 | 3.5 |
| 4 | 2 | 7.1 | 72.1 | 0 | 7.1 |
| 6 | 3 | 6.8 | 76.7 | 7.2 | 7.3 |
| 34 | 4 | 8.4 | 79.7 | 14.3 | 9.8 |
| 71 | 5 | 7.2 | 81.8 | 14.6 | 8.5 |
| 96 | 6 | 6.5 | 80.8 | 15.5 | 7.7 |
| 119 | 7 | 6.3 | 80.6 | 15.1 | 7.4 |
| 643 | 8 | 6.0 | 81.0 | 14.3 | 7.0 |
| 168 | 9 | 5.9 | 80.7 | 14.4 | 6.9 |
| 239 | 10 | 5.0 | 78.2 | 8.8 | 5.5 |
| 263 | 11 | 5.3 | 79.2 | 13.5 | 6.2 |
| 288 | 12 | 5.0 | 79.6 | 16.5 | 6.0 |
| 311 | 13 | 5.4 | 79.4 | 4.1 | 5.6 |
| 335 | 14 | 5.5 | 79.2 | 8.2 | 6.0 |
| 408 | 15 | 4.9 | 79.4 | 13.1 | 5.6 |
| 432 | 16 | 4.7 | 78.8 | 14.4 | 5.5 |
| 456 | 17 | 4.4 | 78.5 | 14.1 | 5.1 |
| 479 | 18[a] | 4.7 | 78.6 | 2.7[b] | 4.8 |
| 488 | 19[b] | 4.9 | 78.5 | 2.4[c] | 5.0 |
| 503 | 20[b] | 5.1 | 78.9 | 0.6[c] | 5.1 |

[a]Corrected for benzene in effluent sample.
[b]Applied pressure 8" $H_2O$
[c]Applied pressure 12" $H_2O$

EXAMPLE 4

This example also illustrates the preparation of linear alkylbenzenes from paraffin dehydrogenate using a hydrogen fluoride-treated mordenite catalyst.

Following the procedures of Example 2, alkylation was conducted in the glassware unit of FIG. 1 complete with catalyst column, reboiler, condenser and controls. To the reaction zone was charged 500 cc of HF-treated mordenite of Example B. The liquid feed comprised a benzene plus $C_{10}$–$C_{14}$ paraffin dehydrogenate mix in a 5:1 molar ratio of benzene /$C_{10}$–$C_{14}$ olefin. The feed rate was 100 cc/hr (LHSV:0.2 hr$^{-1}$).

Under typical steady state, reflux, conditions, with a reboiler temperature range of 131–205° C. and a head temperature of 76–83° C., typical results are summarized in Table 5.

TABLE 5

| Pressure (Inch $H_2O$) | Reboiler Temp. (C.) | Time on Stream (Hrs) | Sample | Alkylate Conc. (%) | 2-Phenyl Sel. (%) | $C_6H_6$ Conc. (%) | Corrected[a] Alkylate Conc. (%) |
|---|---|---|---|---|---|---|---|
| 12 | 205 | 2 | 1 | 8.2 | 74.3 | 0.5 | 8.3 |
|  | 193 | 4 | 2 | 9.2 | 75.0 | 0.4 | 9.2 |
|  | 175 | 6 | 3 | 10.0 | 74.8 | 2.3 | 10.3 |
|  | 204 | 21 | 4 | 12.7 | 78.7 | 0.3 | 12.7 |
|  | 146 | 44 | 5 | 11.7 | 81.0 | 10.4 | 12.9 |
|  | 136 | 68 | 6 | 11.5 | 81.8 | 10.0 | 12.7 |
|  |  | 2–3 days | C[b] | 11.6 | 81.4 | 9.4 | 12.7 |
|  | 136 |  93 | 7 | 11.3 | 82.6 | 10.8 | 12.5 |
|  |  | 4–5 days | C-1[b] | 11.0 | 81.8 | 11.0 | 12.2 |
|  | 142 | 165 | 8 | 10.4 | 83.0 | 11.4 | 11.5 |
|  | 142 | 189 | 9 | 10.2 | 83.4 | 10.5 | 11.2 |
|  | 146 | 213 | 10 | 9.7 | 80.2 | 11.2 | 10.7 |
|  | 139 | 238 | 11 | 9.6 | 83.4 | 11.1 | 10.7 |
|  | 143 | 261 | 12 | 9.9 | 81.9 | 11.0 | 11.0 |
|  | 133 | 333 | 13 | 9.2 | 83.4 | 11.3 | 10.3 |
|  | 138 | 356 | 14 | 8.9 | 83.5 | 11.1 | 9.9 |
|  | 138 | 381 | 15 | 8.8 | 83.0 | 11.3 | 9.8 |
|  | 131 | 405 | 16 | 8.7 | 82.8 | 11.2 | 9.7 |

[a]Corrected for benzene in effluent sample
[b]Composite product

EXAMPLE 5

This example illustrates the preparation of linear alkylbenzenes from paraffin dehydrogenate using a hydrogen fluoride-treated mordenite catalyst.

Following the procedures of Example 2, alkylation of benzene with $C_{10}$–$C_{14}$ paraffin dehydrogenate was conducted using the stainless-steel unit of FIG. 2, complete with catalyst column, reboiler, condenser, and controls. About 250 cc or HF-treated mordenite of Example B was charged to the column. The liquid feed comprised benzene plus $C_{10}$–$C_{14}$ paraffin dehydrogenate mix in a 10:1 molar ratio of benzene/$C_{10}$–$C_{14}$ olefin. The LHSV varied from 0.2 to 0.4 hr$^{-1}$.

Alkylation was conducted over a range of column and reboiler temperatures and a range of exit pressures. Typical results are summarized in Table 6.

TABLE 6

| Column Temp (C.) | Pressure DIFF (psi) | Pressure EXIT (psi) | Pot Temp. (C.) | Time (hr) | Alkylate Sample (#) | Alkylate Conc. (%) | 2-Phenyl Sel. (%) | $C_6H_6$ Conc. (%) |
|---|---|---|---|---|---|---|---|---|
| 149-129 | 0.1 | 0 | 188 | 4 | 1 | 3.8 |  | 6.3 |
| 152-126 | 0 | 0 | 200 | 20 | 2 | 1.8 |  | 32.7 |
| 195-108 | 0 | 0 | 199 | 25 | 3 | 5.7 |  | 8.7 |
| 218-111 | 0 | 0 | 201 | 28 | 4 | 0.8 |  | 67.5 |
| 212-118 | 0 | 0 | 201 | 44 | 5 | 8.8 | 71.7 | 4.5 |
| 209-114 | 0.2 | 0 | 198 | 52 | 6 | 2.4 |  | 47.3 |
| 228-116 | 0 | 0 | 197 | 68 | 7 | 6.9 | 72.6 | 12.4 |
| 187-107 | 0.5 | 0 | 197 | 76 | 8 | 2.9 | 74.6 | 44.1 |
|  |  |  |  | 76 | 9[a] | 4.8 | 72.9 | 25.3 |
|  |  |  |  |  | 9C[b] | 6.8 | 72.2 | 1.0 |
| 174-107 | 0 | 0 | 178 | 6 | 10 | 4.1 | 79.2 | 54.9 |
| 170-106 | 0 | 0 | 172 | 22 | 11 | 2.0 |  | 59.8 |
|  |  |  |  | 28 | 12[a] | 6.6 | 76.8 | 26.8 |
| 142-107 | 0 | 0 | 136 | 31 | 13 | 4.8 | 67.9 | 18.9 |
| 141-110 | 0 | 0 | 138 | 47 | 14 | 4.4 | 65.9 | 16.9 |
| 142-110 | 0 | 0 | 136 | 55 | 15 | 5.0 | 63.9 | 16.6 |
| 168-111 | 0 | 0 | 131 | 71 | 16 | 4.1 | 64.8 | 16.7 |
| 170-108 | 0 | 0 | 150 | 79 | 17 | 5.0 | 72.0 | 8.8 |
| 175-113 | 0 | 0 | 143 | 95 | 18 | 5.9 | 68.1 | 15.2 |
| 145-106 | 0 | 5.2 | 188 | 14 | 19 | 3.2 | 60.2 | 9.0 |
| 149-108 | 0 | 4.2 | 186 | 20 | 20 | 4.8 | 66.3 | 12.0 |
| 160-118 | 0 | 11.7 | 213 | 29 | 21 | 4.2 |  | 6.7 |
| 160-119 | 0 | 9.3 | 210 | 44 | 22 | 5.2 |  | 6.6 |

[a]Composite product
[b]Stripped composite product

EXAMPLES 6–8

These examples illustrate the preparation of linear alkylbenzene using hydrogen fluoride-modified mordenite catalysts with different fluoride treatment levels.

Following the procedures of Example 1, the alkylation unit was charged with benzene (100 ml), a 10 g sample of hydrogen fluoride-modified mordenite prepared by the procedure of Example B, plus a mix of benzene (50 ml) and 1-decene (10 g). Three HF-treated mordenites were tested, having the composition:

Catalyst "C" 0.25% HF on mordenite (CBV-20A)
Catalyst "D" 0.50% HF on mordenite (CBV-20A)
Catalyst "E" 1.0% HF on mordenite (CBV-20A)

In each experiment samples of the bottoms liquid fraction were withdrawn at regular periods and subject to gas chromatography analyses. The results are summarized in Table 7.

TABLE 7

| CATALYST | TIME | %LLAB | %ISOS | %HVY | %2Ph | %3Ph | %4Ph | %5Ph | %6&7Ph |
|---|---|---|---|---|---|---|---|---|---|
| D | 10 | 11.75 | 0.14 | 0 | 73.36 | 21.87 | 2.89 | 0.94 | 1.02 |
|   | 20 | 12.43 | 0.21 | 0 | 72.97 | 21.96 | 3.14 | 1.13 | 0.81 |
|   | 30 | 12.88 | 0.21 | 0 | 72.67 | 22.13 | 3.03 | 1.16 | 1.01 |
|   | 40 | 12.27 | 0.22 | 0 | 73.02 | 21.92 | 2.85 | 1.06 | 1.14 |
|   | 50 | 12.15 | 0.98 | 0 | 72.46 | 21.67 | 3.21 | 1.17 | 1.49 |
|   | 50 | 12.24 | 1.01 | 0 | 72.53 | 21.63 | 3.23 | 1.12 | 1.44 |
|   | 60 | 12.28 | 0.21 | 0 | 72.96 | 22.07 | 2.93 | 1.14 | 0.91 |
|   | 60 | 11.98 | 0.21 | 0 | 72.97 | 22.21 | 2.93 | 1.17 | 0.83 |
| C | 10 | 12.2 | 0.18 | 0 | 72.54 | 22.46 | 3.21 | 0.98 | 0.82 |
|   | 20 | 12.7 | 0.39 | 0 | 71.51 | 22.61 | 2.91 | 1.02 | 2.13 |
|   | 30 | 12.52 | 0.21 | 0 | 71.96 | 22.68 | 2.96 | 1.04 | 1.36 |
|   | 40 | 12.75 | 0.21 | 0 | 71.84 | 22.67 | 3.22 | 1.02 | 1.25 |
|   | 50 | 12.98 | 0.21 | 0 | 71.57 | 22.81 | 3.16 | 1.08 | 1.39 |
|   | 60 | 12.54 | 0.21 | 0 | 71.45 | 22.81 | 3.19 | 1.12 | 1.44 |
|   | 60 | 12.33 | 0.21 | 0 | 71.61 | 22.87 | 2.92 | 1.05 | 1.31 |
| E | 10 | 10.56 | 0.05 | 0 | 75.19 | 19.41 | 2.18 | 3.22 |  |
|   | 20 | 12.95 | 0.15 | 0 | 74.36 | 19.23 | 3.01 | 3.4 |  |
|   | 30 | 13.44 | 0.18 | 0 | 74.11 | 19.42 | 3.2 | 3.27 |  |
|   | 40 | 13.16 | 0.15 | 0 | 074.16 | 19.38 | 3.12 | 3.34 |  |
|   | 50 | 13.1 | 0.15 | 0 | 74.43 | 19.16 | 3.21 | 3.28 |  |
|   | 60 | 12.83 | 0.15 | 0 | 74.28 | 19.49 | 2.88 | 3.35 |  |
|   | 60 | 12.87 | 0.16 | 0 | 73.82 | 19.97 | 2.8 | 3.2 |  |

EXAMPLE 9

This example illustrates the inactivity of a heavily loaded hydrogen-fluoride modified mordenite catalyst.

Following the procedures of Example 2, the alkylation unit was charged with 100 cc of a hydrogen fluoride-treated mordenite (CBV-20A) prepared by the method of Example B but having a much higher loading of HF (fluoride content 4.8%). The acidity of said HF-treated mordenite was 0.15 meq/g.

No significant amount of alkylated product was detected by gas chromatography.

What is claimed is:

1. A process for the production of linear alkylbenzene, comprising:
    contacting benzene and an olefin having about 8 to about 30 carbons in the presence of a fluorine-containing mordenite to form a first linear alkylbenzene stream;
    contacting benzene and an olefin having about 8 to about 30 carbons in the presence of an alkylation catalyst other than the fluorine-containing mordenite to form a second linear alkylbenzene stream;
    combining the first linear alkylbenzene stream and the second linear alkylbenzene stream to form a third linear alkylbenzene stream,
    wherein the mordenite has been treated by contacting the mordenite with an aqueous hydrogen fluoride solution, wherein the hydrogen fluoride in the aqueous solution has a concentration in the range from about 0.1 percent to about 1 percent by weight.

2. The process of claim 1, wherein the olefin is obtained by dehydrogenating a paraffin.

3. The process of claim 1, wherein the third linear alkylbenzene stream is distilled to remove unreacted benzene, olefin and any components heavier than the linear alkylbenzene.

4. The process of claim 1, wherein the fluorine-containing mordenite has a silica to alumina molar ratio in a range from about 10:1 to about 50:1.

5. The process of claim 1, wherein the benzene and olefin that is contacted with mordenite is a slip stream from a stream containing benzene and olefin that is to be contacted with the alkylation catalyst other than the fluorine-containing mordenite.

6. The process of claim 1 which is operated under conditions effective to produce a 2-phenyl isomer content in the third linear alkylbenzene stream in the range from about 30 to about 40 percent by weight.

7. The process of claim 1, wherein the benzene and olefin to be contacted with the mordenite has a benzene/olefin ratio of from about 2:1 to about 20:1, wherein the mordenite is maintained at a temperature in the range from about 70 degrees Centigrade to about 200 degrees Centigrade, and wherein the benzene and olefin that contacts the mordenite has a combined liquid hourly space velocity in the range from about 0.05 $hr^{-1}$ to about 10 $hr^{-1}$.

8. The process of claim 1 wherein the alkylation catalyst other than the fluorine-containing mordenite is hydrogen fluoride.

9. The process of claim 1 wherein the alkylation catalyst other than the fluorine-containing mordenite is aluminum chloride.

10. A process useful for the production of linear alkylbenzene, comprising:
    combining a product from a linear alkylbenzene alkylation reactor that employs a catalyst other than a fluorine-containing mordenite catalyst with a product from a linear alkylbenzene alkylation reactor containing fluorine-containing mordenite,
    wherein the mordenite has been treated by contacting the mordenite with an aqueous hydrogen fluoride solution, wherein the hydrogen fluoride in the aqueous solution has a concentration in the range from about 0.1 percent to about 1 percent by weight.

11. The process of claim 10 wherein the product from the linear alkylbenzene alkylation reactor that employs a catalyst other than a fluorine-containing mordenite catalyst has a 2-phenyl isomer content below about 30 percent by weight and wherein the product of the mordenite reactor has a 2-phenyl isomer content above about 70 percent by weight.

12. The process of claim 10 wherein the linear alkylbenzene alkylation reactor that employs a catalyst other than a fluorine-containing mordenite catalyst is a hydrogen fluoride reactor.

13. The process of claim 10 wherein the linear alkylbenzene alkylation reactor is an aluminum chloride reactor.

14. A process for the production of linear alkylbenzene, comprising:

dehydrogenating a paraffin to form an olefin;

sending a primary feed stream of benzene and the olefin through a conduit to an alkylation reactor;

contacting the primary feed stream in the alkylation reactor with an alkylation catalyst other than a fluorine-containing mordenite catalyst under conditions effective to react the benzene and olefin to form a first linear alkylbenzene product;

withdrawing a portion of the primary feed stream from the conduit and contacting the portion with a fluorine-containing mordenite under conditions effective to react the benzene and olefin to form a second linear alkylbenzene product;

combining the first and second linear alkylbenzene products to form a crude linear alkylbenzene stream;

distilling the crude linear alkylbenzene stream in a first distillation column to separate benzene that did not react and to form a benzene-free linear alkylbenzene stream;

optionally distilling the benzene-free linear alkylbenzene stream in a second distillation column to separate any olefin and to form an olefin free linear alkylbenzene stream;

distilling the olefin free alkylbenzene stream in a third distillation column to provide an overhead of a purified linear alkylbenzene product and removing a bottoms stream containing any heavies, wherein the mordenite has been treated by contacting the mordenite with an aqueous hydrogen fluoride solution, wherein the hydrogen fluoride in the aqueous solution has a concentration in the range from about 0.1 percent to about 1 percent by weight.

15. The process of claim 14 further comprising recycling the benzene from distillation of the crude linear alkylbenzene stream to the conduit.

16. The process of claim 14 further comprising dewatering the portion of the primary feed stream prior to contact with the fluorine-containing mordenite.

17. The process of claim 14 wherein the alkylation catalyst other than a fluorine-containing mordenite catalyst is a hydrogen fluoride.

18. The process of claim 14 wherein the alkylation catalyst other than a fluorine-containing mordenite catalyst is aluminum chloride.

* * * * *